United States Patent [19]

Miller

[11] 4,248,229
[45] Feb. 3, 1981

[54] ENEMA TIP RETENTION APPARATUS

[76] Inventor: Roscoe E. Miller, 7400 W. 88th St., Indianapolis, Ind. 46278

[21] Appl. No.: 39,280

[22] Filed: May 16, 1979

[51] Int. Cl.³ .............................................. A61M 3/00
[52] U.S. Cl. ............................. 128/245; 128/DIG. 26
[58] Field of Search ............... 128/245, 248, DIG. 26, 128/348, 350, 247, 98, 341, 351

[56] References Cited

U.S. PATENT DOCUMENTS

| 2,586,940 | 2/1952 | Graham | 128/DIG. 26 |
|---|---|---|---|
| 2,908,269 | 10/1959 | Cheng | 128/DIG. 26 |
| 3,154,078 | 10/1964 | Goodrich | 128/348 |
| 3,408,092 | 10/1968 | Appleton | 285/39 |
| 3,429,985 | 2/1969 | Czigler | 174/164 |
| 3,516,631 | 1/1970 | Santucci | 248/71 |
| 3,543,744 | 12/1970 | Le Par | 128/2 |
| 3,575,160 | 4/1971 | Vass et al. | 128/2 R |
| 3,581,732 | 6/1971 | Ruiz | 128/2 R |
| 3,760,811 | 9/1973 | Andrew | 128/351 |
| 3,765,401 | 10/1973 | Vass | 128/1 R |
| 3,802,418 | 4/1974 | Clayton | 128/2 F |
| 3,841,304 | 10/1974 | Jones | 128/1 R |
| 3,893,446 | 7/1975 | Miller | 128/2 A |
| 3,906,948 | 9/1975 | Vass | 128/245 |
| 3,993,081 | 11/1976 | Cussell | 128/351 |
| 4,069,826 | 1/1978 | Sessions et al. | 128/348 |

Primary Examiner—John D. Yasko
Attorney, Agent, or Firm—Woodard, Weikart, Emhardt & Naughton

[57] ABSTRACT

An enema tip retention apparatus for retaining an inserted enema tip in a patient during the administering of an enema to the patient includes an adjustable belt for encompassing the waist of the patient and including depending straps which couple to a substantially flat mounting plate. The mounting plate has a clamp disposed thereon and a clearance aperture therethrough and includes two collar buttons which are arranged for connection to the two depending straps. The clamp has a ratcheted arrangement such that its clearance aperture diameter may be varied, depending upon the enema tube outside diameter which is inserted therethrough. With the depending straps coupled to the collar buttons, the mounting plate may be drawn adjacent the rectal opening of the patient and with the enema tip and tube anchored by the clamp, this tip and tube may be held in position throughout a fluoroscopy examination and will be retained in its desired position, regardless of the movements and the maneuvers the patient is subjected to.

13 Claims, 12 Drawing Figures

ENEMA TIP RETENTION APPARATUS

Background of the Invention

An enema tip retention apparatus for retaining an inserted enema tip in a patient during the administering of an enema to the patient includes an adjustable belt for encompassing the waist of the patient and including two depending straps which couple to a substantially flat mounting plate. The mounting plate has an adjustable, releasable clamp disposed thereon and a first clearance aperture therethrough. The mounting plate further includes two collar buttons which are arranged on opposite sides of the releasable clamp for connection to the two depending straps. The clamp includes a second clearance aperture extending therethrough and defined by a part-circular portion, a deformable tab portion and cooperating locking portion. The tab portion and locking portion are arranged relative to each other such that the second clearance aperture diameter may be varied, depending upon the outside diameter of the enema tube which is inserted therethrough. The first and second clearance apertures are substantially coincident with each other. With the depending straps coupled to the collar buttons, the mounting plate may be drawn adjacent the rectal opening of the patient and with the enema tip and tube anchored by the clamp, this tip and tube may be held in position throughout a fluoroscopy examination and will be retained in its desired position, regardless of the movements and the maneuvers the patient is subjected to.

Most radiologists have had barium spill on the examining table when they conduct colon examinations of incontinent, seriously ill and hard-to-manage patients. Such patients include the mentally retarded, the mentally ill, the aged, the uncooperative, the severely handicapped, the paraplegic and the patient with an extremely relaxed anal canal. One problem with such patients involves their inability to retain an enema tip which is inserted for the administration of a diagnostic contrast medium for either cleansing or medication purposes. The enema tip frequently slips out because of the turning of the patient and the various maneuvers required, after the barium has been introduced, as part of the fluoroscopy X-ray examination.

One retention technique which has often been employed is to insert and then inflate a balloon on either or on both sides of the rectum. However, some physicians object to these balloons because of the dangers of perforation or over inflation. Therefore, it would be an improvement to enema tip retention devices and procedures if a means and structure could be devised to securely hold an enema tip in position without reliance on inflatable balloons. A further improvement would be to structure such a device so that it would be suitable for use with remotely controlled fluoroscopy tables where the operator (technician and/or physician and/or radiologist) is some distance from the patient. A retention device such as the suggested improved device is beneficial in that such attending medical personnel do not have to hold the device in the patient while X-rays are taken and subject themselves to additional radiation exposure.

Various retention techniques have been conceived as set forth by the disclosures of the following listed patents. However, none of these disclosures set forth a device with advantages equal to the advantages of the present invention to be described in detail hereinafter. Thus, the present invention is an improvement to all prior art devices of which the inventor is aware.

| U.S. Pat. No. | Patentee | Issue Date |
|---|---|---|
| 3,543,744 | LePar | 12/01/70 |
| 3,575,160 | Vass | 4/20/71 |
| 3,581,732 | Ruiz | 6/01/71 |
| 3,841,304 | Jones | 10/15/74 |
| 3,893,446 | Miller | 7/08/75 |
| 3,906,948 | Vass | 9/23/75 |
| 4,069,826 | Sessions et al. | 1/24/78 |
| 3,802,418 | Clayton | 4/09/74 |
| 3,765,401 | Vass | 10/16/73 |
| 3,408,092 | Appleton | 10/29/68 |
| 3,154,078 | Goodrich, Jr. | 10/27/64 |
| 3,429,985 | Czigler | 2/25/69 |
| 3,516,631 | Santucci | 6/23/70 |

LePar discloses equipment for administering enemas, particularly for radiological purposes and includes an obturator which is adapted to be positioned externally of the body in the region of an intestinal opening. The obturator is flexible and distendable or inflatable. The equipment further includes an annular sealing element at the interface of the obturator which is adapted to provide a liquid-tight seal between the obturator and the surface of the body in the region around the intestinal opening.

Vass U.S. Pat. No. 3,575,160 discloses an instrument for administering fluid into the intestinal tract, which includes a tube having a rectum entering end portion and enlargements distally of the end portion which are engageable against the body area surrounding the anal opening of the rectum and entering thereinto for sealing the same when the end portion is disposed within the rectum.

Ruiz discloses a device for conveying fluids, such as aqueous suspensions of barium sulfate, into and out of a body opening such as a colostomy opening, and includes conduit means, a radial flange integral with the conduit means, pressure means for maintaining the flange in direct contact with a stoma, base means for engaging the abdominal wall and body-encircling means for maintaining the base means in place.

Jones discloses an inflatable balloon-like bulb attached to the end of a check-valved catheter tube which is removably attachable to an inflating bulb and further includes stop means slidable along the catheter tube. This arrangement is such that when the balloon is deflated on the end of the catheter tube, it may be inserted through the urethra into the bladder, and then inflated by the bulb and held in that position by the sliding stop pushed up against the urethral outlet walls to hold the inflated balloon in sealing relationship.

Miller discloses a catheter structure for insertion in an opening of a body and includes a support member which is frictionally slidable along the catheter to a desired position. The support member portion which enters the body as an annular extension engaged by an adhesive patch which extends beyond the annular extension and may engage the skin of the body in order to position the catheter. A closure member is also provided for the outer end of the catheter in order to prevent loss of contents of inserted material until such time as the closure member is removed.

Vass U.S. Pat. No. 3,906,948 discloses a rectal applicator for the administration of an enema as practiced in the roentgen examination of the intestinal tract and includes a device formed by joining a tubular nozzle section with a tubular stem section. The device is provided at the junction of its two sections with an enlargement, the proximal face of which is formed with concentric annular ridges spaced from the nozzle tube and one another and is engageable against the perianal surface of a body to seal externally the anal opening.

Sessions et al. discloses a surgical tube adapter clamp for effecting a tube connection to a blood vessel in which a tubular member is constructed for insertion of its free end into a blood vessel and the opposite end is adapted to be operatively connected to the cooperable end of the tube. A pair of relatively deformable members are provided and encircle the tubular member such that one of said deformable members is adapted to be disposed adjacent the exterior wall of the blood vessel and the other member includes a portion disposed within the blood vessel which is adapted to be deformed to increase the effective diameter thereof within the blood vessel and thereby clamp the adjacent wall of such blood vessel between the deformable members to secure the clamp to the vessel.

Clayton discloses a colon catheter for removing and collecting waste colon material through the anal canal. One end of a hollow tube is inserted into the anal canal and held therein by an expandable member and limiting elements outside of the anal opening against the perineum.

Vass U.S. Pat. No. 3,765,401 discloses a belt for sustaining an article in site in the rectal or uro-genital area formed by a waist-surrounding band having independent dorsal and frontal aprons laterally adjustably held thereon and a bridge which is engageable against the article to be held by the ends of the aprons.

Appleton discloses a single-piece tubular connector for connecting one end of a length of flexible hose to other apparatus and includes a central flanged tubular body separating a preferably externally threaded hose end from another end which is also threaded but preferably with oppositely-handed threads.

Goodrich, Jr. discloses a catheter combination which includes a fluid-containing squeeze-bulb syringe which has a discharge end securely bonded to an inflating tube in order to form a fluid-tight connection. The squeeze-bulb syringe is preloaded with the desired kind of inert fluid in the exact amount desired for the size and type of balloon employed so that the fluid is sealed into the system and cannot escape or become contaminated. A clip guard is provided about the syringe in order to prevent accidental squeezing of the syringe, and this clip guard is ratcheted so that the syringe may be held in partially collapsed positions and thereby prevent the undesired return of fluid.

Czigler discloses an adjustable clamp for elongated articles and includes a substantially rigid base member, a substantially rigid inverted J-shaped locking member extending upwardly from the base member and a deformable tab which may be flexible extending upwardly from the base member. Cooperating locking means on the locking member and flexible tab are adapted to inter-engage and releasably lock the clamp.

Santucci discloses a cable clamp device for mounting one or more cables on a suitable substructure. The clamp is provided with adhesive or mechanical means for securing the clamp to a substructure. The cable clamp includes at least a pair of legs which cooperate with the base member to provide a cable enclosure. This enclosure is open initially for the installation of a cable and can then be locked to positively retain the cable or cables.

SUMMARY OF THE INVENTION

An enema tip retention apparatus for retaining an inserted enema tip in a patient during the administering of an enema according to one embodiment of the present invention comprises a mounting plate, enema tube attachment means joined to said mounting plate and having a clearance aperture disposed therethrough, strap means securable to the body of the patient and having a retaining portion positionable adjacent the patient's rectum and retaining means joined to the mounting plate and disposed on opposite sides of the attachment means, the retaining means being suitably arranged for connection to the retaining portion of the strap means.

One object of the present invention is to provide an improved enema tip retention apparatus.

Related objects and advantages of the present invention will be apparent from the following description.

BRIEF DESCRIPTION OF THE DRAWINGS

FIG. 3 is a front elevation view of an alternative clamp device also suitable for use with alternative arrangements of the FIG. 1 enema tip retention apparatus and the like.

DESCRIPTION OF THE PREFERRED EMBODIMENT

Figure 1:
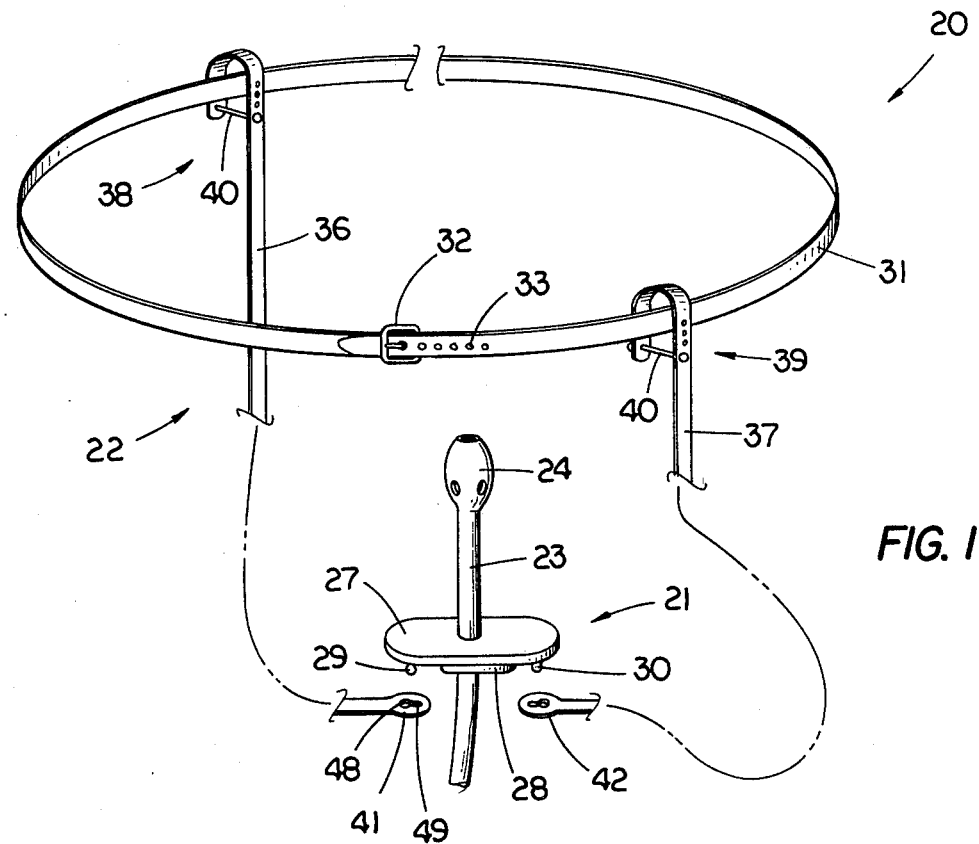
FIG. 1 is an exploded perspective view of an enema tip retention apparatus according to a typical embodiment of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1, there is illustrated an enema tip retention apparatus 20 including clamp member 21, adjustable belt arrangement 22, enema tube 23 and enema tip 24. Clamp member 21 includes a mounting plate portion 27 adjustable, releasable clamp 28 and collar buttons 29 and 30 which provide retaining means for securing clamp member 21 to adjustable belt arrangement 22.

Figure 7:
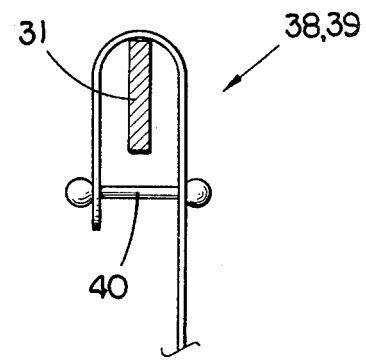
FIG. 7 is a partial side elevation view of adjustable strap means comprising a portion of the FIG. 1 and FIG. 6 enema tip retention apparata.

Belt arrangement 22 includes a first strap portion 31 which is variable in circumferential encompassing size by means of belt buckle 32 and adjustment holes 33. Looped around first strap portion 31 are retaining straps 36 and 37 whose length extension from first strap portions 31 in a downwardly direction is controlled by adjustment means 38 and 39. Adjustment means 38 and 39 (see FIG. 7) include a collar stickpin-type arrangement wherein the outermost enlarged end portions of pin 40 are inserted through strap holes and thereby disposed on opposite outwardly facing surfaces of their corresponding retaining straps. This arrangement securely forms an enclosing loop for each strap which surrounds first strap portion 31.

The free ends of retaining straps 36 and 37 each include a keyhole-shaped slot 41 and 42, respectively, which are suitably sized and arranged for engagement with and receipt of collar buttons 29 and 30. Collar buttons 29 and 30 (see FIGS. 1a and 2) each include a base portion 45, an enlarged head portion 46 and a reduced diameter portion 47 therebetween. The size and shape of collar buttons 29 and 30 is such that enlarged head portion 46 is able to pass through larger opening 48 of keyhole-shaped slots 41 and 42 but not the smaller oblong opening portion 49. Thus, the means of attachment of clamp member 21 to adjustable belt arrangement 22 is to insert collar buttons 29 and 30 into keyhole-shaped slots 41 and 42 and then pull outwardly on retaining straps 36 and 37 such that reduced diameter portions 47 are snugly anchored within smaller oblong openings 49, and retained there due to the larger sizes of head portion 46 and base portion 45.

Figure 1A:
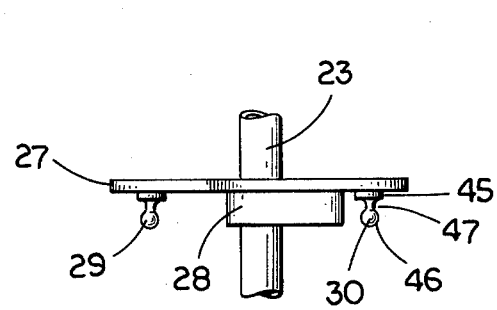
FIG. 1a is a front elevation view of a clamp device comprising a portion of the FIG. 1 enema tip retention apparatus.
Figure 2:
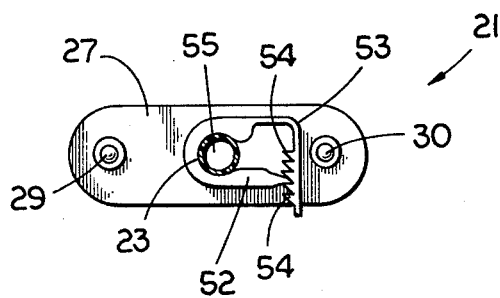
FIG. 2 is a bottom plan view of the FIG. 1a clamp device.

Referring to FIG. 2, clamp member 21 is illustrated in greater detail and includes a deformable tab portion 52, a cooperating locking portion 53, which has a series of ratchet teeth 54, and a clearance aperture 55 located adjacent the common end of portions 52 and 53. Clearance aperture 55 extends through clamp member 21, including mounting plate portion 27. Enema tube 23 is partially shown in both FIG. 1a and FIG. 2 illustrations and is disposed within clearance aperture 55. As deformable tab portion 52 and cooperating locking portion 53 are drawn together, by squeezing, the dimensional size of clearance aperture 55 is reduced, and a clamping action occurs around enema tube 23 thereby holding this tube in position. Inasmuch as the longitudinal axis of clearance aperture 55 is substantially perpendicular to mounting plate portion 27, it should be apparent that when clamp member 21 is oriented near the rectal opening of a patient and first strap portion is secured around the patient's waist, that retaining straps 36 and 37 may be adjusted in length until clamp member 21 is drawn snugly up against the patient's rectal opening so that the enema tube 23 and its joined enema tip 24 are retained in position within the patient. By securing the enema tube and tip in such a manner, the enema tip is unable to slip out of the patient as the patient turns from one side to the other and orients his body in various positions which the radiologist or physician may request as part of the fluoroscopy X-ray examination procedure.

Figure 3:
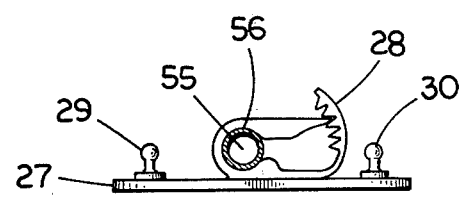
Figure 4:
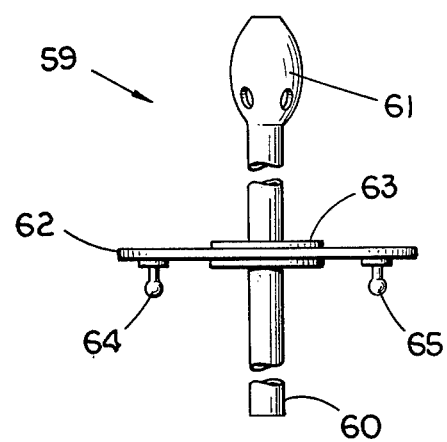
FIG. 4 is a partial front elevation view of an alternative clamp device including enema tip and tube portions joined therewith.
Figure 5:
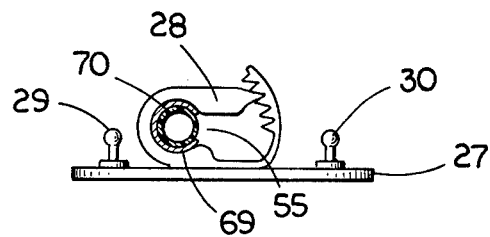
FIG. 5 is a front elevation view of yet another alternative clamp device also suitable for use with alternatives of the FIG. 1 enema tip retention apparatus.

Referring to FIGS. 3, 4 and 5, alternative arrangements of clamp member 21 are illustrated. While it should be understood that the preferred arrangement of clamp member 21 with respect to the remainder of apparatus 20 is to have the smooth surface of mounting plate portion 27 closest to the patient, it is possible to use an orientation wherein the collar button side of mounting plate portion 27 is closest to the patient. It is also possible to arrange adjustable, releasable clamp 28 such that the longitudinal axis of its clearance aperture is parallel with the surface of mounting plate portion 27 rather than being perpendicular to it. FIG. 3 illustrates such an arrangement where clamp 28 is disposed on mounting plate portion 27 so that the longitudinal axis of clearance aperture 55 is substantially parallel with the surface of mounting plate portion 27. Also included is a tube 56 which is shown in section only and secured by clamp 28. This tube may be a drainage tube or similar device and thus, the arrangement of FIG. 3 is suitable for retaining such tubes in a fixed position so that drainage of the patient cavities can be achieved, such as the sinuses. While this particular arrangement may not be best suited for enema administering, the clamping concept is virtually the same as clamp member 21 and collar buttons 29 and 30 are provided for retention of this alternative clamp member when such drainage of cavities is desired to be achieved.

Referring to FIG. 4, there is illustrated a clamp, enema tube and enema tip combination 59 which is a one-piece, integral, molded assembly. Combination 59 includes an enema tube 60, an enema tip 61, a mounting plate 62, a clearance hole grommet 63, collar button 64 and collar button 65. Although fabricated as a molded, one-piece combination, it is possible that these various component parts could be individually molded and then fitted together in a press-fit manner such that grommet 63 would be anchored within mounting plate 62 and would provide a snug fit around the outside diameter of enema tube 60 such that the tube and tip 61 would be held securely in position within the patient. In this manner, collar buttons 64 and 65 would be utilized as has been previously explained for collar buttons 29 and 30 of FIG. 1.

Referring to FIG. 5, the alternative clamp member of FIG. 3 is illustrated and includes a tubular insert 69 which has a lateral cross section of a "C" shape. This insert is generally concentric with clearance aperture 55 and is suitable to adapt the inside diameter size of clearance aperture 55 to the outside diameter of tube 70 such that various-sized tubes can be held by the clamp member. All that is required for adaptation is to select the appropriately sized C-shaped insert with the desired thickness. The use of such inserts is also envisioned with clamp member 21 inasmuch as the orientation of the clamp 28 with respect to the mounting plate portion 27, whether parallel or perpendicular, is equally well suited for the addition of such inserts.

Figure 8:
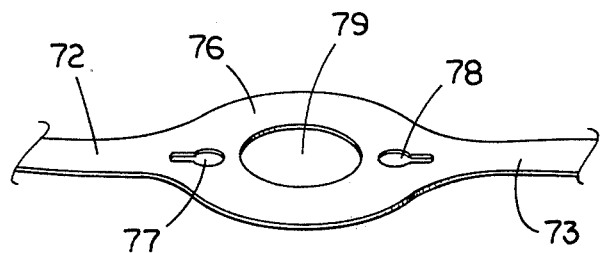
FIG. 8 is a partial perspective view of a retaining portion comprising a part of the FIG. 6 enema tip retention apparatus.
Figure 6:
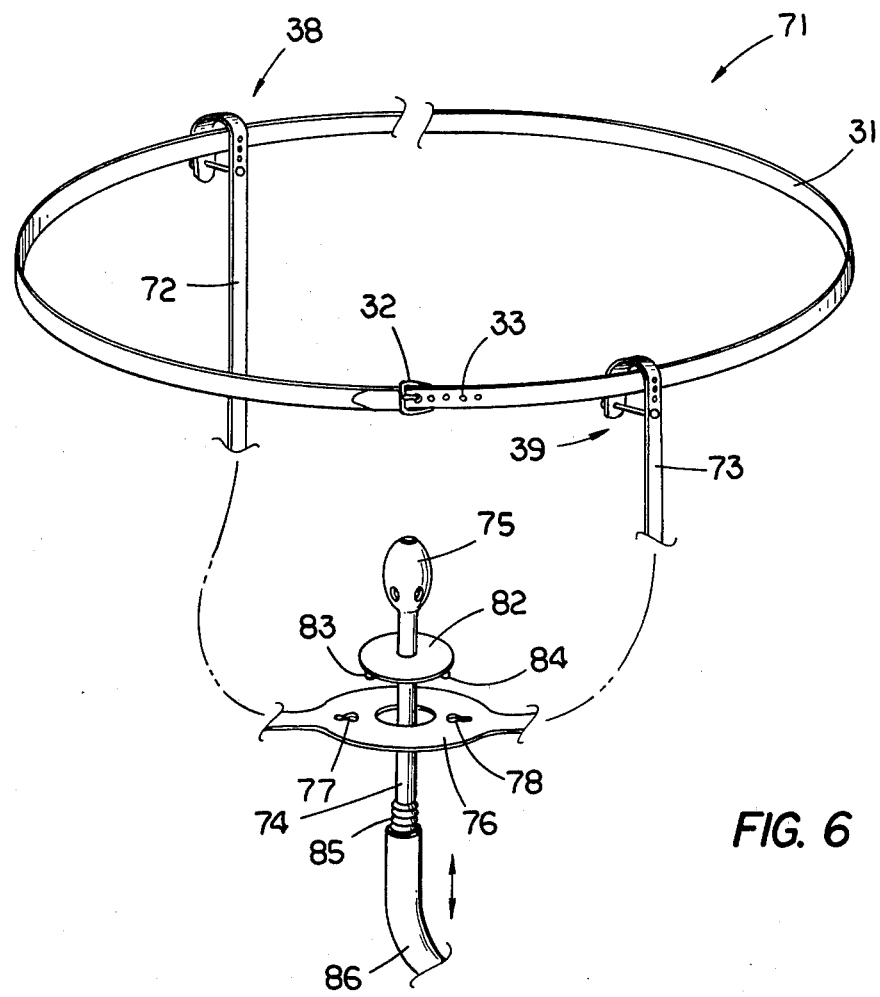
FIG. 6 is an exploded perspective view of an enema tip retention apparatus according to a typical embodiment of the present invention.

Referring to FIG. 6 an alternative arrangement of the FIG. 1 apparatus is illustrated and although belt arrangement 71 is similar to belt arrangement 22, the noted difference involves the design of retaining straps 72 and 73 which are joined together at the general location of the enema tube 74 and enema tip 75 by means of retaining portion 76. Retaining portion 76 serves virtually the same purpose as did the free ends of retaining straps 36 and 37 which were provided with keyhole-shaped slots 41 and 42, respectively. In the FIG. 6 illustration, keyhole-shaped slots 77 and 78 (see FIG. 8) are provided and the only difference between the retaining portion arrangement of FIG. 1 and that of FIG. 6 is that the two retaining straps 72 and 73 are joined together wherein their Y-shaped configuration and union at two locations creates a clearance opening 79. Enema tube 74 and enema tip 75 are joined together and extend through a retaining flange 82 which includes two oppositely disposed collar buttons 83 and 84 which are suitably positioned and sized to fit within keyhole-shaped slots 77 and 78. In order to insert retaining flange 82 into retaining portion 76, the outer ends of flange 82 must be drawn together by bending flange 82 and then insert collar buttons 83 and 84 into the enlarged opening portions of slots 77 and 78. By fabricating retaining flange 82 out of a resilient, flexible material, release from this bent position will cause the collar buttons to flip outwardly thereby locking them in position in the smaller oblong opening portions of slots 77 and 78. This locking engagement securely retains the enema tube and enema tip as part of belt arrangement 71. The free end of enema tube 74 is provided with a series of angularly arranged layers or serrations 85 and these provide a snug fit arrangement with flexible tube 86 which may be forced over the free end of enema tube 74. Tube 86 may then be connected to a source of barium for introduction into the patient.

Figure 9:
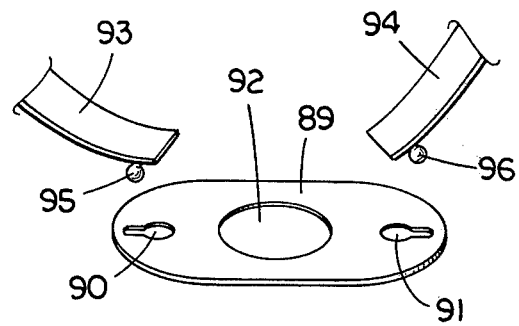
FIG. 9 is an exploded perspective view of an alternate retaining portion arrangement suitable for use with the FIG. 6 enema tip retention apparatus.

Referring to FIG. 9, an alternative arrangement to the retaining portion designs of FIGS. 1 and 6 is illustrated. Retaining flange 89 is a separate component and includes keyhole-shaped slots 90 and 91 and a clearance opening 92. Retaining straps 93 and 94 are provided with collar buttons 95 and 96, respectively, disposed at their free ends. As has been previously described, collar buttons 95 and 96 are arranged to be received by slots 90 and 91 for fixed retention of retaining flange 89. The clearance opening 92 of retaining flange 89 is suitably sized to receive in a snugly-fit arrangement an enema tip and tube combination or similar tubular member.

Figure 10:
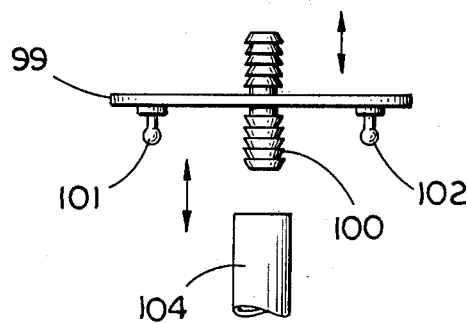
FIG. 10 is an exploded front elevation view of enema tube attachment means suitable for use with the FIG. 1 and FIG. 6 enema tip retention apparata.
Figure 11:
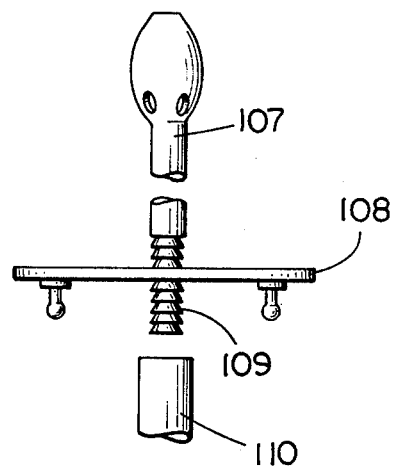
FIG. 11 is an exploded front elevation view of alternative enema tube attachment means similarly suitable for use with the FIG. 1 and FIG. 6 enema tip retention apparata.

Referring to FIGS. 10 and 11, still further alternative arrangements are illustrated. In FIG. 10, mounting plate 99 is provided with a serrated tubular member 100 secured therethrough as well as collar buttons 101 and 102. Serrated tubular member 100 extends beyond each surface of mounting plate 99 a distance sufficient for the connection of enema tip 103 and enema tube 104. By fabricating the enema tip and enema tube members out of a flexible resilient material, they may be easily axially forced over the extending portions of serrated tubular member 100 and firmly lock onto the serrated surfaces, thereby providing a fixed and integrally appearing arrangement.

In FIG. 11, the enema tip 107 is secured to mounting plate 108 and has a free end 109 of a serrated tube design. In this arrangement, enema tube 110 will fit over the extending serrations of free end 109 and although the enema tip and mounting plate are an integral design, various enema tubes may be used in this particular combination.

Although a conventional enema tip and enema tube combination have been illustrated throughout this specification, it is to be understood that the retaining and clamping arrangements disclosed herein are equally suitable for use with various types and styles of enema tips and tubes, including, but not limited to, those disclosed in my copending patent application, Ser. No. 39,502, filed on May 16, 1979 now abandoned. Thus the arrangements disclosed herein are suitable for double-contrast studies in which air is introduced after the barium is evacuated. In fact, the arrangements disclosed in the specification are particularly well suited to such double-contrast studies in that the enema tube and tip can be retained within the patient throughout the study in a well-secured and comfortable manner and is not subject to slipping out or otherwise separating from its inserted position within the patient. Thus, in combination with any of one the various barium and air combination tubes of my copending patent application, barium is first introduced and then evacuated and then air is subsequently introduced into the patient and all of these operations may be performed without the necessity to remove the enema tip from the patient.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An enema tip retention apparatus for retaining an inserted enema tip in a patient during the administering of an enema to the patient, and thereafter as desired for fluoroscopy examinations as well as repeated enema administering, said enema tip retention apparatus comprising:

a substantially flat mounting plate having a patient-facing surface and an opposite exterior surface and a first clearance aperture therethrough;

enema tube attachment means including a single-piece, adjustable, releasable clamp joined to said mounting plate on said exterior surface and having a second clearance aperture disposed therethrough, said second clearance aperture being substantially coincident with said first clearance aperture, said releasable clamp includes a part-circular enclosing portion defining a part of said second clearance aperture and extending on one side into a deformable tab portion and extending on the opposite side into a locking portion cooperatively arranged with said deformable tab portion for varying the size of said second clearance aperture;

strap means securable to the body of the patient and having a retaining portion positionable adjacent the patient's rectum; and retaining means joined to said mounting plate and disposed on opposite sides of said releasable clamp, said retaining means being suitably arranged for connection to the retaining portion of said strap means.

2. The enema tube retention apparatus of claim 1 wherein said releasable clamp includes a tubular insert having a C-shaped transverse cross section and being disposed substantially concentric with said clearance aperture.

3. An enema tip retention apparatus for retaining an inserted enema tip in a patient during the administering of an enema to the patient, and thereafter as desired for fluoroscopy examinations as well as repeated enema administering, said enema tip retention apparatus comprising:
- a mounting plate;
- enema tube attachment means including an adjustable, releasable clamp joined to said mounting plate and having a clearance aperture disposed therethrough and being defined by a deformable tab portion and a cooperating locking portion wherein the longitudinal axis of said clearance aperture extends in a direction substantially parallel to the surface of said mounting plate;
- strap means securable to the body of the patient and having a retaining portion positionable adjacent the patient's rectum; and
- retaining means joined to said mounting plate and disposed on opposite sides of said enema tube attachment means, said retaining means being suitably arranged for connection to the retaining portion of said strap means.

4. An enema tip retention apparatus for retaining an inserted enema tip in a patient during the administering of an enema to the patient, and thereafter as desired for fluoroscopy examinations as well as repeated enema administering, said enema tip retention apparatus comprising:
- a substantially flat mounting plate having a patient-facing surface and an opposite exterior surface and a first clearance aperture therethrough;
- enema tube attachment means including a single-piece, adjustable, releasable clamp joined to said mounting plate on said exterior surface and having a second clearance aperture disposed therethrough, said second clearance aperture being substantially coincident with said first clearance aperture, said second clearance aperture having a longitudinal axis which extends in a direction substantially perpendicular to the surface of said mounting plate;
- strap means securable to the body of the patient and having a retaining portion positionable adjacent the patient's rectum; and
- retaining means joined to said mounting plate and disposed on opposite sides of said releasable clamp, said retaining means being suitably arranged for connection to the retaining portion of said strap means.

5. The enema tip retention apparatus of claim 4 wherein said retaining means includes raised button members each having an enlarged uppermost portion and being suitable for retained engagement within a keyhole-shaped slot.

6. The enema tip retention apparatus of claim 5 wherein said strap means includes a belt which is adjustable in its circumferential encompassing size and two depending strap portions whose length is adjustable for the locating of said retaining portion, said retaining portion including a plurality of keyhole-shaped slots.

7. An enema tip retention apparatus for retaining an inserted enema tip in a patient during the administering of an enema to the patient, and thereafter as desired for fluoroscopy examinations as well as repeated enema administering, said enema tip retention apparatus comprising:
- a mounting plate;
- enema tube attachment means integrally molded with said mounting plate and having a clearance aperture disposed therethrough;
- strap means securable to the body of the patient and having a retaining portion positionable adjacent the patient's rectum;
- retaining means joined to said mounting plate and disposed on opposite sides of said enema tube attachment means, said retaining means being suitably arranged for connection to the retaining portion of said strap means; and
- an enema tube and tip secured to said mounting plate by said enema tube attachment means.

8. An enema tip retention apparatus for retaining an inserted enema tip in a patient during the administering of an enema to the patient, and thereafter as desired for fluoroscopy examinations as well as repeated enema administering, said enema tip retention apparatus comprising:
- a mounting plate;
- enema tube attachment means integrally molded with said mounting plate and including a serrated tube portion, said serrated tube portion defining a clearance aperture disposed through said enema tube attachment means;
- strap means securable to the body of the patient and having a retaining portion positionable adjacent the patient's rectum; and
- retaining means joined to said mounting plate and disposed on opposite sides of said enema tube attachment means, said retaining means being suitably arranged for connection to the retaining portion of said strap means.

9. The enema tip retention apparatus of claim 8 wherein said serrated tube portion extends sufficiently through said mounting plate so as to provide a serrated length suitable for connection to flexible tubing.

10. The enema tip retention apparatus of claim 8 which further includes an enema tube and enema tip and wherein said serrated tube is integrally connected with the end of said enema tip.

11. An enema tip retention apparatus for retaining an inserted enema tip in a patient during the administering of an enema to the patient, and thereafter as desired for fluoroscopy examinations as well as repeated enema administering, said enema tip retention apparatus comprising:
- a mounting plate;
- enema tube attachment means including an adjustable, releasable clamp joined to said mounting plate and having a clearance aperture disposed therethrough, said clearance aperture being defined by a deformable tab portion and cooperating locking portion, and the longitudinal axis of said clearance aperture extending in a direction substantially perpendicular to the surface of said mounting plate;
- strap means securable to the body of the patient and having a retaining portion positionable adjacent the patient's rectum; and
- retaining means joined to said mounting plate and disposed on opposite sides of said enema tube attachment means, said retaining means being suitably arranged for connection to the retaining portion of said strap means, said retaining means including a plurality of keyhole-shaped slots each being suitable for retained engagement with raised button members having enlarged head portions.

12. The enema tip retention apparatus of claim 11 wherein said retaining portion includes two securing straps, each strap having at least one raised button member.

13. An enema tip retention apparatus for retaining an inserted enema tip in a patient during the administering of an enema to the patient, and thereafter as desired for fluoroscopy examinations as well as repeated enema administering, said enema tip retention apparatus comprising:

a mounting plate;

enema tube attachment means including an adjustable, releasable clamp joined to said mounting plate and having a clearance aperture disposed therethrough and being defined by a deformable tab portion and a cooperating locking portion, said releasable clamp further including a tubular insert having a C-shaped transverse cross-section and being disposed substantially concentric with said clearance aperture, said cooperating locking portion being ratcheted with a series of teeth and said deformable tab portion governing the transverse cross-sectional area of said clearance aperture depending upon the particular tooth engaged;

strap means securable to the body of the patient and having a retaining portion positionable adjacent the patient's rectum; and retaining means jointed to said mounting plate and disposed on opposite sides of said enema tube attachment means, said retaining means being suitably arranged for connection to the retaining portion of said strap means.

* * * * *